US011718868B2

(12) United States Patent
Medintz et al.

(10) Patent No.: US 11,718,868 B2
(45) Date of Patent: Aug. 8, 2023

(54) NANOPARTICLE-BASED LIPASE BIOSENSOR UTILIZING A CUSTOM-SYNTHESIZED PEPTIDYL-ESTER SUBSTRATE

(71) Applicant: The Government of the United States of America, as represented by the Secretary of the Navy, Arlington, VA (US)

(72) Inventors: Igor Medintz, Washington, DC (US); Joyce A. Breger, Washington, DC (US); Kimihiro Susumu, Washington, DC (US); Sebastian Diaz, Washington, DC (US); Jesper Brask, Lyngby (DK)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 321 days.

(21) Appl. No.: 17/161,889

(22) Filed: Jan. 29, 2021

(65) Prior Publication Data

US 2021/0238650 A1 Aug. 5, 2021

Related U.S. Application Data

(60) Provisional application No. 62/968,746, filed on Jan. 31, 2020.

(51) Int. Cl.
| | | |
|---|---|---|
| *C12Q 1/44* | (2006.01) | |
| *C12Q 1/34* | (2006.01) | |
| *C09K 11/56* | (2006.01) | |
| *G01N 21/64* | (2006.01) | |
| *C09K 11/88* | (2006.01) | |

(52) U.S. Cl.
CPC .............. *C12Q 1/44* (2013.01); *C09K 11/565* (2013.01); *C09K 11/883* (2013.01); *C12Q 1/34* (2013.01); *G01N 21/6428* (2013.01); *G01N 2021/6439* (2013.01)

(58) Field of Classification Search
CPC ........... C12Q 1/44; C12Q 1/34; C09K 11/565
See application file for complete search history.

(56) References Cited

U.S. PATENT DOCUMENTS

| 8,409,858 B2 | 4/2013 | Delehanty et al. | |
| 10,416,144 B2 * | 9/2019 | Troyer | C12Q 1/37 |

FOREIGN PATENT DOCUMENTS

| WO | WO-2004013348 A2 * | 2/2004 | C12Q 1/34 |
| WO | WO-2005040412 A1 * | 5/2005 | C12Q 1/34 |

OTHER PUBLICATIONS

Freeman, R., Finder, T., & Willner, I. (2009). Multiplexed analysis of Hg2+ and Ag+ ions by nucleic acid functionalized CdSe/ZnS quantum dots and their use for logic gate operations. Angewandte Chemie, 121(42), 7958-7961. (Year: 2009).*
Algar, W. R., A. P. Malanoski, K. Susumu, M. H. Stewart, N. Hildebrandt and I. L. Medintz (2012). "Multiplexed Tracking of Protease Activity Using a Single Color of Quantum Dot Vector and a Time-Gated Förster Resonance Energy Transfer Relay." Analytical Chemistry 84(22): 10136-10146.
Algar, W. R., A. Malonoski, J. R. Deschamps, J. B. Banco-Canosa, K. Susumu, M. H. Stewart, B. J. Johnson, P. E. Dawson and I. L. Medintz (2012). "Proteolytic Activity at Quantum Dot-Conjugates: Kinetic Analysis Reveals Enhanced Enzyme Activity and Localized Interfacial "Hopping"." Nano Letters 12(7): 3793-3802.
Sapsford, K. E., D. Farrell, S. Sun, A. Rasooly, H. Mattoussi and I. L. Medintz (2009). "Monitoring of enzymatic proteolysis on a electroluminescent-CCD microchip platform using quantum dot-peptide substrates." Sensors and Actuators B-Chemical 139(1): 13-21.
Peter Fojan, Per H Jonson, Maria T.N Petersen, Steffen B Petersen, "What distinguishes an esterase from a lipase: A novel structural approach," Biochimie, vol. 82, Issue 11, 2000, pp. 1033-1041.

\* cited by examiner

*Primary Examiner* — Robert J Yamasaki
*Assistant Examiner* — Trevor L Kane
(74) *Attorney, Agent, or Firm* — U.S. Naval Research Laboratory; Roy Roberts

(57) ABSTRACT

Lipase activity can be detected with a biosensor that includes a quantum dot adhered to a construct having a lipase-cleavable ester to attach a fluorophore acceptor configured as a Förster resonance energy transfer (FRET) acceptor to the QD when the construct is bound thereto. Cleavage of the ester by a lipase results in a measurable reduction in FRET. In further embodiments, the cleavable ester can be used to detect esterase activity, or the ester could be replaced with a glycosidic linkage to detect glycoside activity.

7 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: synthetic construct

<400> SEQUENCE: 1

His His His His His His Ser Gly Pro Pro Pro Pro Pro Pro Asn
1               5                   10                  15

Arg Asp Arg Asp Glu Asp Arg Glu Asp
            20                  25

<210> SEQ ID NO 2
<211> LENGTH: 10
<212> TYPE: PRT
<213> ORGANISM: Artificial Sequence
<220> FEATURE:
<223> OTHER INFORMATION: synthetic construct

<400> SEQUENCE: 2

Asn Arg Asp Arg Asp Glu Asp Arg Glu Asp
1               5                   10
```

NANOPARTICLE-BASED LIPASE BIOSENSOR UTILIZING A CUSTOM-SYNTHESIZED PEPTIDYL-ESTER SUBSTRATE

CROSS-REFERENCE TO RELATED APPLICATIONS

This application claims the benefit of U.S. Provisional Patent Application No. 62/968,746 filed on Jan. 31, 2020, incorporated herein by reference in its entirety for the purposes of teaching techniques for making and using nanoparticle-based lipase biosensors.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 112,187

BACKGROUND

Lipases are a class of esterase enzymes with numerous roles including those in cell biology, food digestion, and in the virulence of specific pathogens. They are also gaining increased commercial interest in such processes as biocatlyzed chemical conversion based on their inherent ability to hydrolyze lipids. Commercial interest in lipases extends to industrial food preparation, pretreatment of cellulosic feedstocks in (bio)fuels preparation, and as additives in many detergents, along with many other applications.

A need exists for specific and sensitive assays to monitor and quantitate lipase activity.

BRIEF SUMMARY

As described herein, nanoparticles (NPs) such as photoluminescent semiconductor quantum dots (QDs) are employed in lipase assays. The below examples feature photoluminescent QDs and a custom-synthesized ester substrate comprising a peptide at one end and a dye-acceptor at the other, thus serving as a nanoscale lipase biosensor. Metal coordination with the Zn-rich surface of the QD and the terminal hexahistidine motif of the peptide allows these ester substrate peptides to ratiometrically self-assemble to the QD surface. This results in a high rate of Förster resonance energy transfer (FRET) between the QD and the proximal substrate's dye-acceptor. Lipase activity can be detected by the hydrolysis of the target ester bond in the substrate, which causes the displacement of the dye-containing component, altering the rate of FRET in a concentration dependent manner. Enzyme characteristics can be determined using an integrated Michaelis-Menten kinetic approach.

In one embodiment, a biosensor includes a quantum dot (QD) and at least one construct adhered to the QD, wherein the construct comprises a nanoparticle association domain, a fluorophore acceptor configured as a Förster resonance energy transfer (FRET) acceptor to the QD when the construct is bound thereto, and a cleavable ester positioned between the nanoparticle association domain and the fluorophore acceptor, wherein cleavage of the ester results in dissociation of the QD and the fluorophore acceptor and thus a change in FRET activity.

In another embodiment, a method of measuring lipase activity involves contacting a sample with a biosensor according to the first embodiment; measuring any change in biosensor fluorescence following the contacting; and correlating the change to esterase (for example, lipase) activity.

In further embodiments, the cleavable ester is replaced with a glycosidic linkage to detect glycoside activity.

BRIEF DESCRIPTION OF THE DRAWINGS

FIG. 4A provides normalized absorption and PL emission of the 520 nm emitting QD donor sample (quantum yield~0.25) and the AlexaFluor 546 (AFF546) acceptor dye utilized in this example. FIG. 4B shows a representative calibration curve where 520 QD donors were assembled with the indicated average ratios of AFF546 dye acceptor-labeled peptide substrate. The −6 sample indicates the acceptor-only sample at the same concentration as the ratio of 6. Samples were excited at 430 nm which corresponds to an acceptor absorption minima. FIG. 4C is a representative plot of the ratio of acceptor PL monitored at 573 nm vs. donor PL collected at 520 nm for the data in FIG. 4B. These data act as the calibration curve that allows the conversion of changes in FRET efficiency during a lipase assay to be converted to units of activity.

DETAILED DESCRIPTION

Definitions

Figure 1:
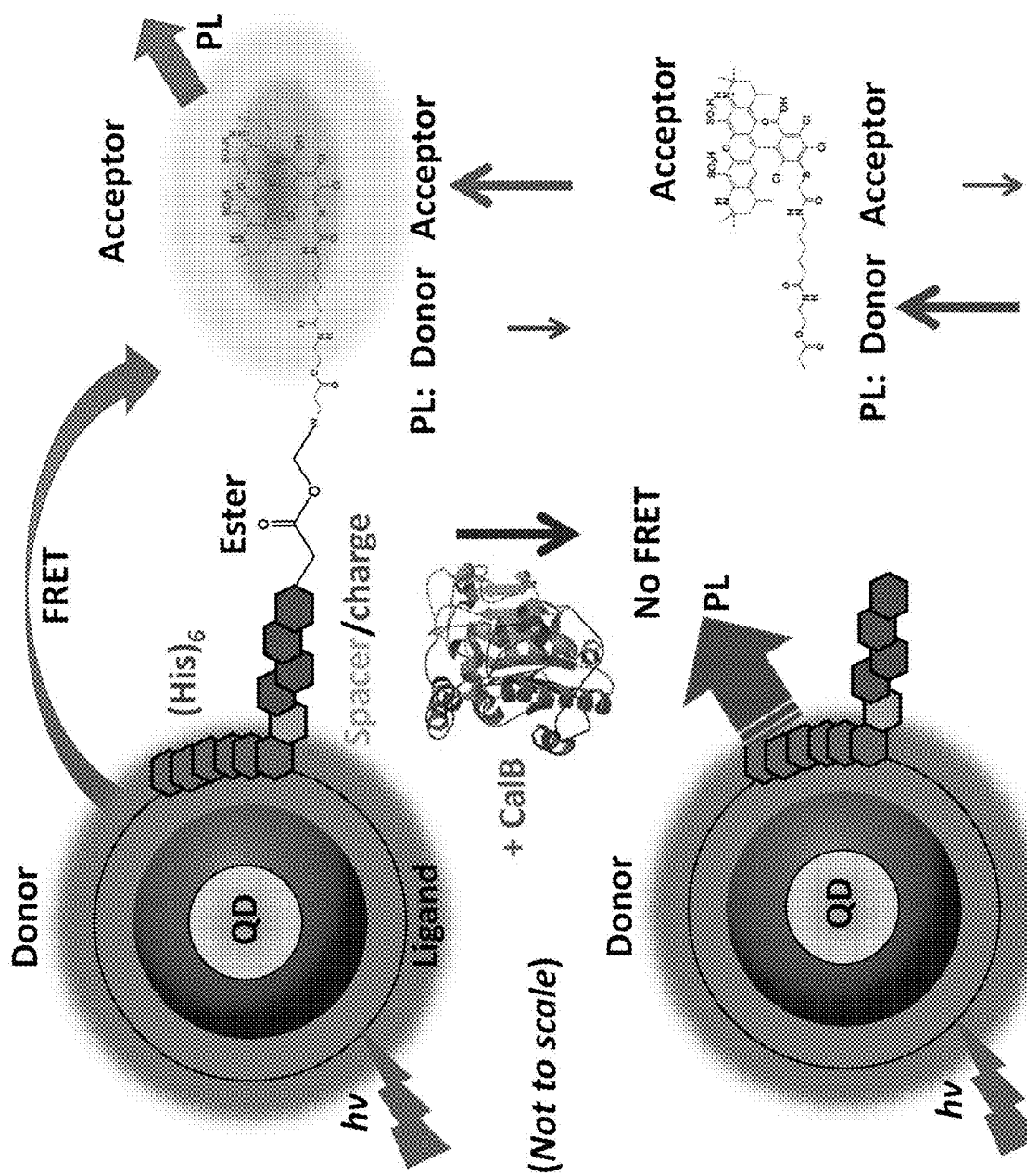
FIG. 1 schematically illustrates an exemplary QD-lipase biosensor. The sensor comprises a semiconductor QD self-assembled with an ester-containing construct. The central QD acts as an exciton donor and assembly scaffold for displaying the ester substrate. The substrate comprises a modular peptide with a nanoparticle association domain, in this case a terminal $(His)_6$ for metal affinity coordination to the QD surface, and a spacer and a charged sequence. Appended to this is the target ester recognized and cleaved by the lipase followed by a dye acceptor. Upon excitation, the QD transfers energy to the acceptor dye by FRET, resulting in a decrease in QD PL and an increase in acceptor sensitized PL. FRET efficiency can be modulated by the number of peptido-acceptors ratiometrically assembled around the QD. Lipase B cloned from *Candida antarctica* (CalB) cleaves the ester allowing it to diffuse away which alters FRET, this decreases acceptor sensitization and increases QD donor PL.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Terms such as "connected," "attached," "linked," and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each sub-combination of the elements of that combination is also specifically disclosed and is within the scope of the invention. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide. The peptides that can be used as described herein include multiple amino acids, which may be natural, synthetic or a mixture thereof. Each peptide may express different side chains, if desired. Other amide oligomers such as beta peptides, peptoids and peptide nucleic acids may also be used.

The terms "semiconductor nanocrystal," "SCNC," "SCNC nanocrystal," "quantum dot," and "QD" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). A given QD sample will have a range of sizes that is characterized by a low range of dispersity or a range of low polydispersity.

A QD is capable of emitting electromagnetic radiation upon excitation (i.e., the QD is luminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate.

The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbSe, and an alloy or a mixture thereof. Preferred shell materials include ZnS.

A QD is optionally surrounded by a "coat" of an organic capping agent. The organic capping agent may be any number of materials, but has an affinity for the QD surface. In general, the capping agent can be an isolated organic molecule, a polymer (or a monomer for a polymerization reaction), an inorganic complex, or an extended crystalline structure. The coat can be used to convey solubility, e.g., the ability to disperse a coated QD homogeneously into a chosen solvent, functionality, binding properties, or the like. In addition, the coat can be used to tailor the optical properties of the QD.

Thus, the quantum dots herein include a coated core, as well as a core/shell QD.

The term "nanoparticle" as used herein includes the above-mentioned QDs in addition to other nano-scale and smaller particles such as carbon nanotubes, proteins, polymers, dendrimers, viruses, and drugs. A nanoparticle has a size of less than about 1 micron, optionally less than about 900, 800, 700, 600, 500, 400, 300, 100, 80, 60, 50, 40, 30, 20, 10, 9, 8, 7, 6, 5, 4, 3, 2, or 1 nanometers. A nanoparticle may have various shapes such as a rod, a tube, a sphere, and the like. Nanoparticles may be made from various materials including metals, carbon (such as carbon nanotubes), polymers, and combinations thereof. A nanoparticle for cytosolic delivery by a peptide may be referred to as a cargo or payload.

The QDs as well as other nanoparticles, may be biofunctionalized for use in, for example, in vivo tissue and cellular labeling, development of biological labels based on quantum dot probes and biosensor development. Other uses of the biofunctionalized materials may include protein ordering for molecular electronics where quantum dots could serve as fluorophores and electronic components, energy harvesting, quantum dot based bar coding, and drug discovery assays where the fluorescence properties of the quantum dots may be combined with bioactive peptides.

The functionalization may be used to impart a variety of properties to quantum dots and/or nanoparticles including, but not limited to, the ability to homogeneously disperse the quantum dots and/or nanoparticles in buffer solutions and a variety of polar solvents at various pH values; biocompatibility; biotargeting by allowing the use of peptide-driven binding to specific cell receptors such as the TAT sequence; providing specific points of modification directly on the quantum dot substrate by using, for example, amine groups for reacting with N-hydroxysuccinimide esters; providing bio-recognized sequences such as the AviTag sequence which is specifically biotinylated as an example; providing protease-recognized cleavage sites; providing polyhistidines for metal affinity coordination; and providing functional groups for further targeted modification, including, for example, amino groups, carboxyl groups, azide groups, alkyne groups, hydrazine groups, aldehyde groups, aminooxy groups, ketone groups, maleimide groups or thiol groups for dye/quencher or other chemical modification steps.

Overview

A Förster resonance energy transfer (FRET)-based biosensor includes a nanoparticle (such as a quantum dot or QD) and a purpose-made esterase substrate which displays a peptide at one end and a dye-acceptor on the other. The substrate can be ratiometrically self-assembled to nanoparticles, for example to luminescent semiconductor QD donors by metal affinity coordination using the appended peptide's terminal hexahistidine motif, yielding the full biosensing construct. In the presence of lipase, the substrate is hydrolyzed at the ester bond location which in turn displaces the dye-containing component altering the FRET signal in a concentration-dependent manner.

Aspects of this work are described in "Quantum Dot Lipase Biosensor Utilizing a Custom-Synthesized Peptidyl-Ester Substrate," Breger et al., *ACS Sens.* 2020, 5, 5, 1295-1304, Feb. 25, 2020 and accompanying Supporting Information, hereinafter referred to as Breger et al., 2020.

Examples

CdSe/CdZnS/ZnS core/shell/shell 520 nm emitting QDs were synthesized and cap-exchanged with compact ligand CL4 as described in Breger et al., 2020, incorporated herein by reference for the purposes of disclosing techniques for preparing and using biosensor constructs such as those described herein.

Figure 2:
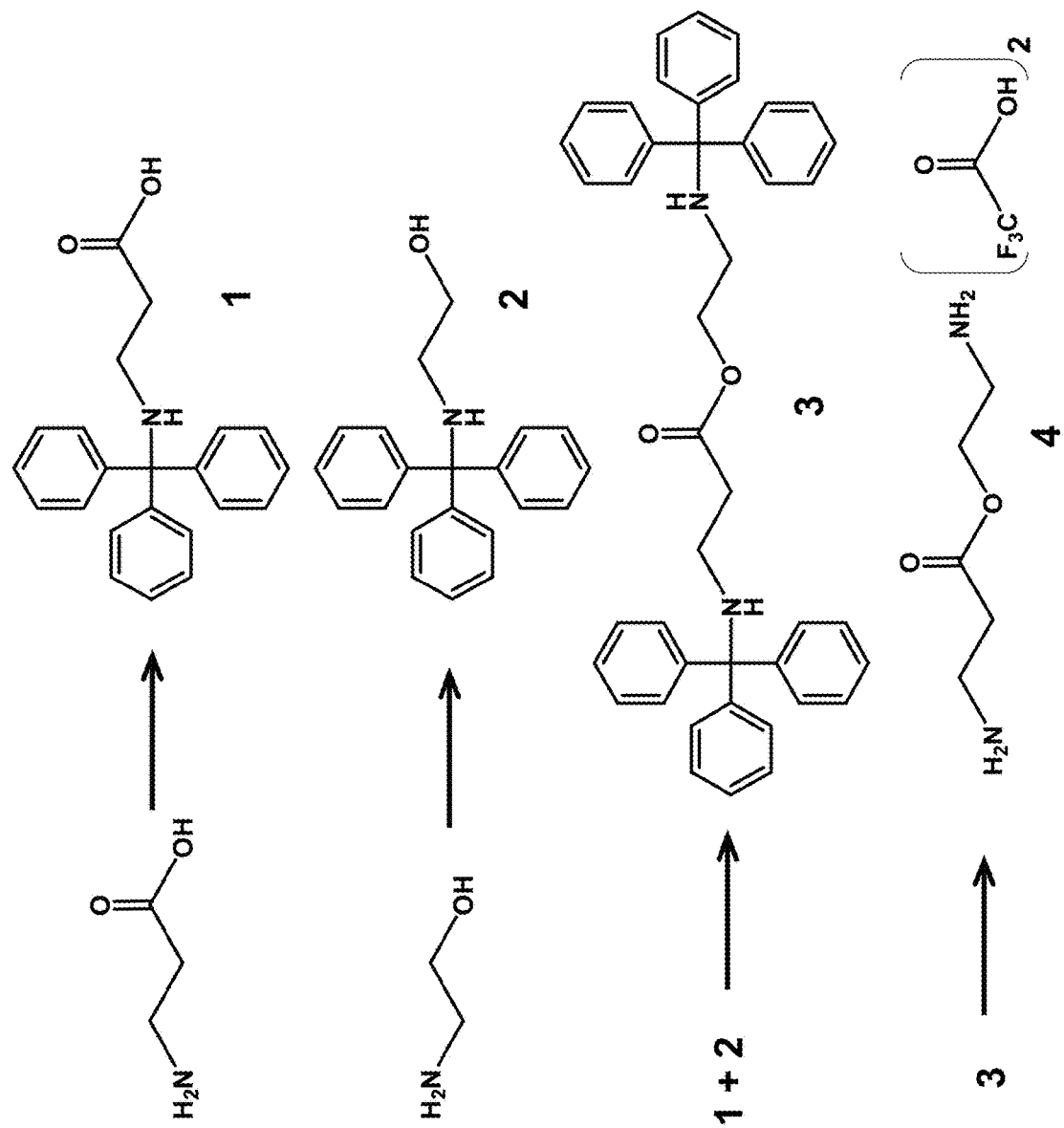
FIG. 2 shows steps in the production of the diamino ester (alternately termed "diaminoester"), with synthetic intermediaries and end ester product. This is the core substrate unit incorporated between the peptide and the dye as part of the substrate chemical assembly.

As illustrated in FIG. 2, a diamino ester (compound 4) was prepared via a series of chemical steps. Further details regarding the synthesis are found in Breger et al., 2020.

Figure 3:
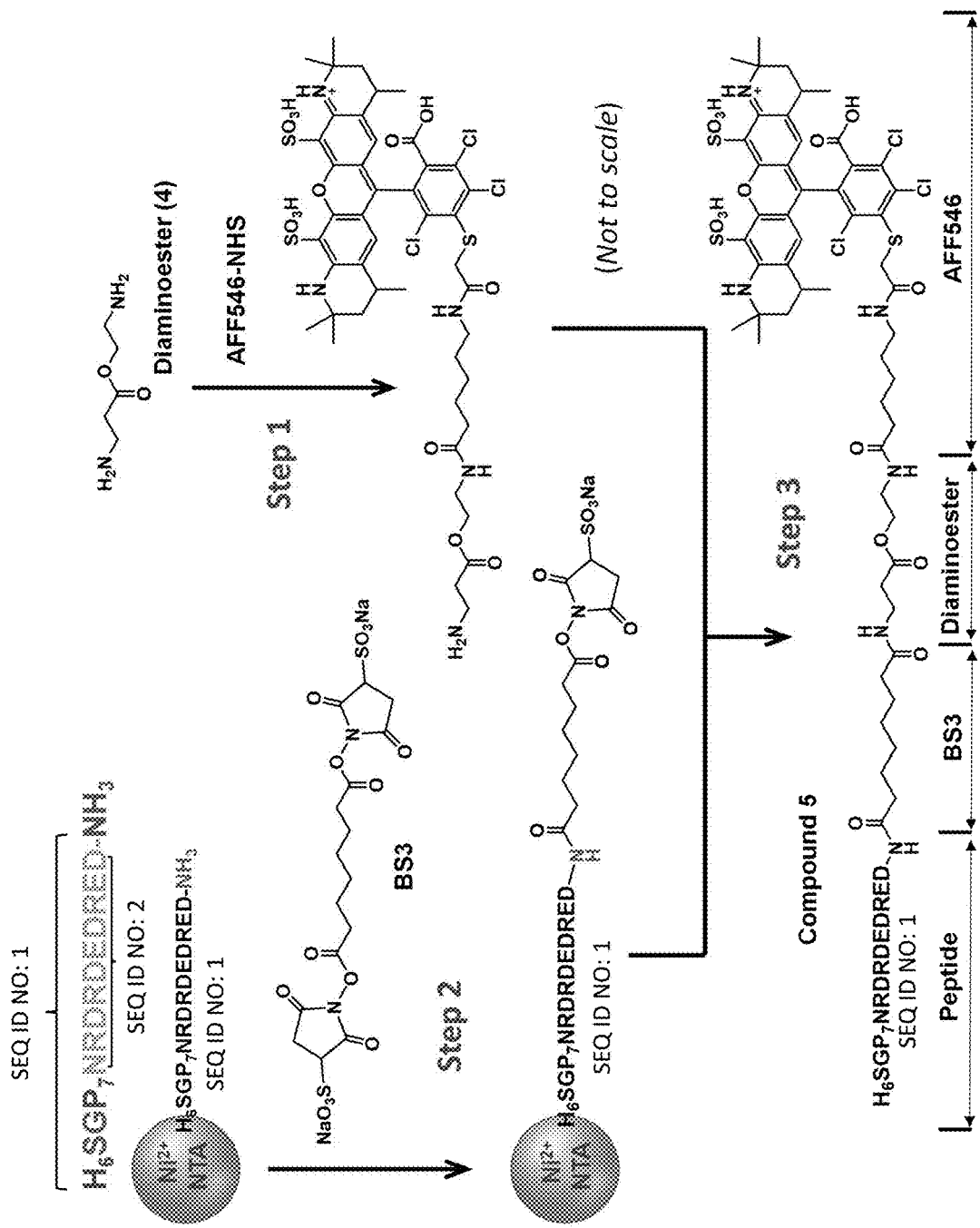
FIG. 3 depicts chemical assembly of the exemplary construct of an acceptor dye-labeled ester-containing peptide-substrate.
Figures 4A, 4B, 4C:
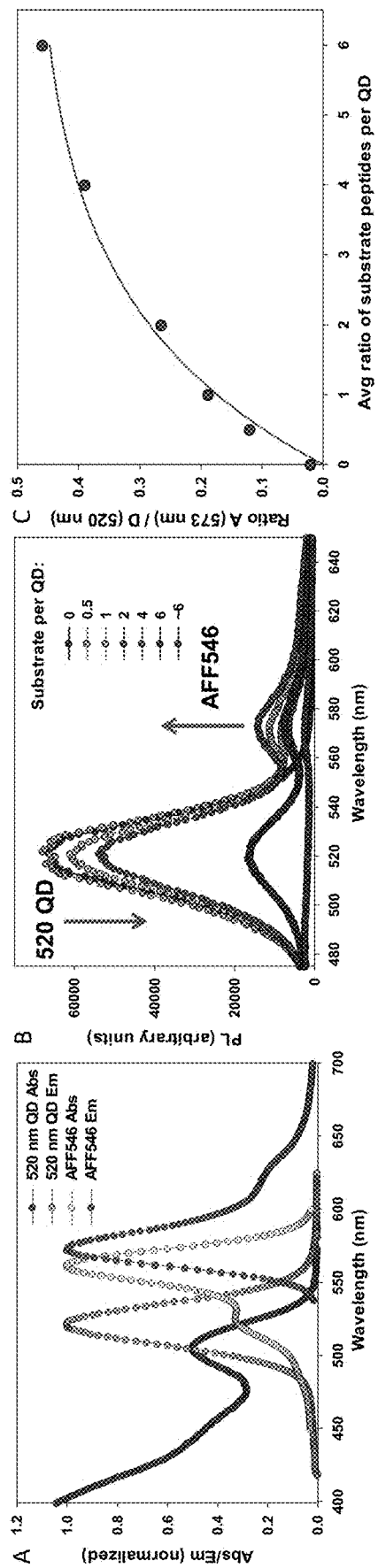
FIGS. 4A-4C show photophysical properties and calibration curves.
Figure 5:
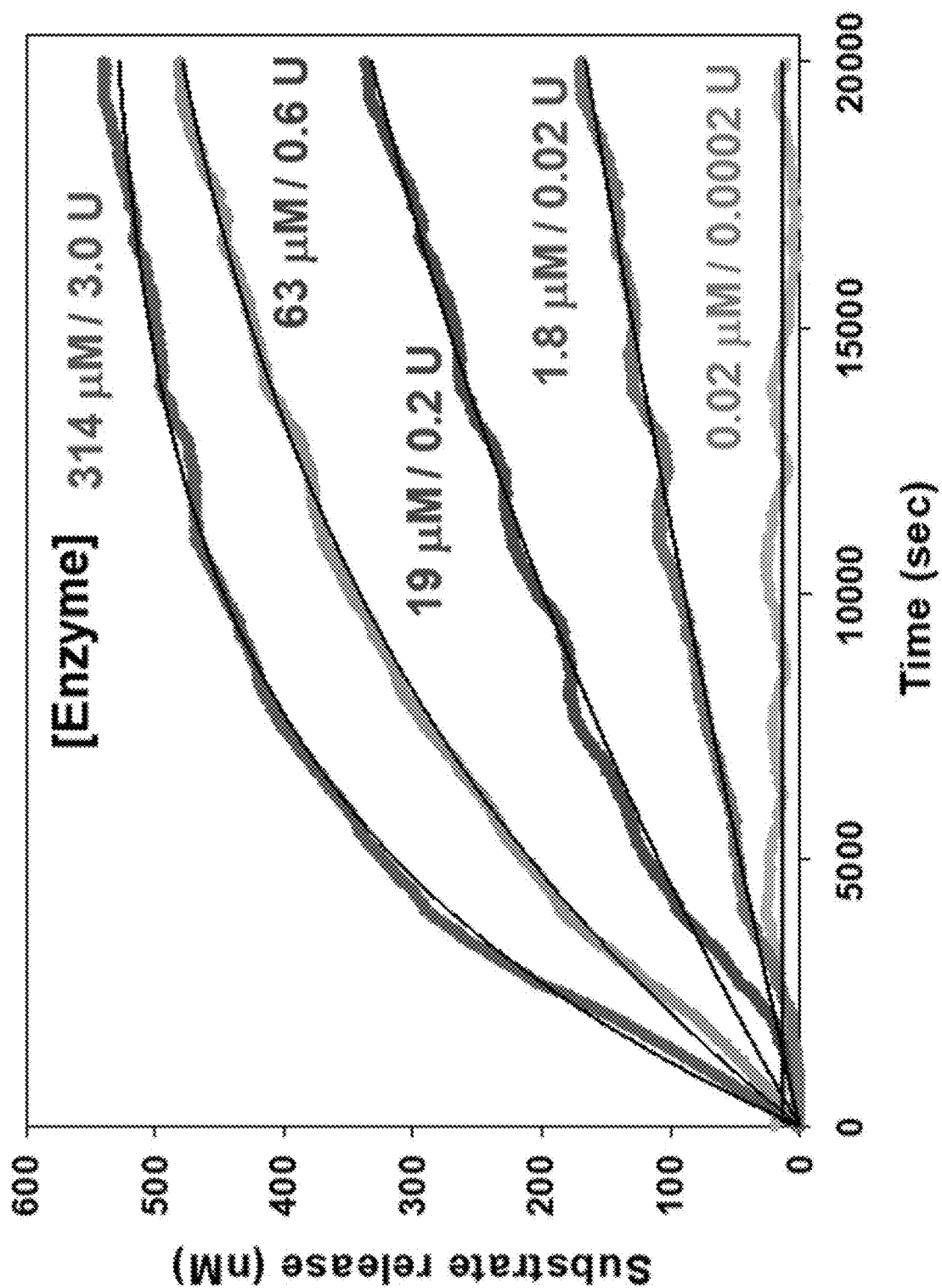
FIG. 5 depicts progress curves from a lipase assay with the QD-peptide ester substrate. 520 QDs were assembled with an average ratio of 4 AFF546 acceptor labeled peptidyl substrates per QD and assayed against increasing concentrations of CalB ranging from 0.02 up to 314 µM over time as indicated. The corresponding number of units of CalB present per assay are shown in the plot. The ratio of AFF546 acceptor to QD donor PL were converted to overall substrate release using the calibration curve in FIG. 3C.

Using this diamino ester, a construct of an acceptor dye-labeled ester-containing peptide-substrate was made as shown in FIG. 3. In Step 1 (top right), the diamino ester (compound 4) is first labeled with an acceptor dye on one of its constituent primary amines. An NHS-activated AlexaFluor 546 dye (AFF546) is utilized in this case with UPLC-MS used to confirm labeling and purify the mono-labeled product. In step 2, a modular, multifunctional peptide with the sequence HHHHHHSGPPPPPPPPNRDRDEDRED-NH3 (shown C- to N-terminal) (SEQ ID No: 1) is used. There, the 116 (blue) serves as the nanoparticle association domain which operates to bind the peptide to a metallic nanoparticle such as a QD, SG (purple) is a flexible linker, P7 (green) is a rigid type II helix, NRDRDEDRED (SEQ ID NO: 2) (orange) is a charged sequence meant to mimic the cell surface, and the unique N-terminal primary amine (red) that is modified in the subsequent chemistry. The peptide is first loaded onto $Ni^{2+}$-NTA resin and then activated with homobifunctional bis(sulfosuccinimidyl)suberate (BS3) on its terminal primary amine to, in turn, display a sulfo-NHS reactive group. Step 3 depicts that, following removal of excess BS3 and washing, the acceptor dye-labeled ester is passed over the BS3-activated peptide repeatedly to yield the final construct, peptide-ester-dye substrate shown on the bottom. Correct assembly is confirmed by MS analysis and, following UPLC purification, the final product was quantitated, and lyophilized.

Aliquots of dye-labeled peptide substrate were dissolved in 10 μL DMSO, then added to 90 μL of assay buffer consisting of 0.1 M $NaH_2PO_4$, 0.1 M NaCl pH 4.2, and 0.6% w/w Triton X-100. Stock solutions of the QD sensor construct were typically prepared as follows: for each individual assay point 25 pmol of 520 nm CL4 QDs were added to 100 pmol of dye-labeled substrate (ratio of 4 dye-labeled peptide substrates per QD) and allowed to assemble on ice for at least one hour in assay buffer.

A dilution curve of lipase was made from a stock solution consisting of 1093 units (U)/mL lipase in buffer. The lipase in these assays was Lipase B cloned from *Candida antarctica* (CalB) and recombinantly expressed in *Aspergillus oryzae* as obtained from SIGMA-ALDRICH with a specific activity of 11.8 Units (U) per mg where 1 U corresponds to the amount of enzyme that functionally liberates 1 mmol butyric acid per minute at pH 8.0 and 40° C. from a tributyrin substrate. The 4-nitrophenyl palmitate (NPPL) lipase substrate was also obtained from SIGMA-ALDRICH. Utilizing a 384-well plate, 14 μL of lipase containing solution was added to each well such that the final concentration of lipase ranged in increments from 0.0002 U up to 3 U (0.02 μM to 314 μM). Prior to starting the kinetic experiment, 11 μL of QD-construct was added to each well of lipase to a final volume of 25 μL with QD at 0.11 μM (2.75 pmol QD/11 pmol construct). The plate was immediately inserted in the TECAN SPARK plate reader and a kinetic cycle initiated consisting of an interval time of 30 sec, exciting at 430 nm and measuring the fluorescence at 520 nm (QD donor) and 573 nm (AFF546 acceptor). Assay temperature was maintained at 30° C. To analyze the results, the ratio of the acceptor and the donor was determined at each time point for each lipase condition. This ratio was then converted to picomoles of dye-labeled peptide substrate cleaved from the QD utilizing a comparative calibration curve. The calibration curve was prepared by assembling dye-labeled peptide substrate to 520 nm CL4 QD in buffer ranging in ratio from 0 to 6 in a similar manner as that described above.

Advantages

The described technique provides a number of advantages.

Luminescent QDs and other NPs can be easily functionalized with a wide variety of surface ligands that provide different surface charges, polarities, steric bulk, etc. which serve to chemically influence the nature of the environment surrounding the NP.

The lipase peptidyl substrates were synthesized with specific modular functionality including a polyhistidine sequence for metal affinity coordination to the QD surface, a spacer, and then a charged sequence. Appended to the peptide was a target ester which can be recognized and cleaved by the lipase and then a dye acceptor. This modular design allows for peptide reconfiguration as needed by a given biosensing format.

Lipase peptidyl substrates can be bound to the QD surface through a simple hexahistidine tag, which can be incorporated terminally of the peptide.

Many other types of bioconjugation chemistry are available for attaching the substrate to a NP including thiol attachment to a gold NP or biotin-avidin interactions, for example. The substrate molecule can be chemically modified during synthesis to accommodate these designs.

The ability to host and display multiple copies of substrate molecules on the QD in a dense, localized format that is reminiscent of how lipids are found on cell surfaces.

Due to the increased density of substrates on the NP scaffold surface, the sensitivity of the assay is increased over single-substrate probe systems. Additionally again due to the relatively increased local density of substrates there is evidence that the lower the enzyme concentration the greater the relative activity of the reporter.

Further Embodiments

In additional embodiment, the cleavable could be replaced with a glycosidic linkage (such as a disaccharide) in order to detect activity of glycosidases. For example, glycosidic linkage can incorporate an α or β linkage in order to detect α or β amylase activity.

The NPs used can be made of practically any material and of any required size and shape. Moreover, one can control the number of substrates displayed around a given NP.

Colloidal NPs (such as QDs) can potentially stabilize the colloidal display of long chain or complex lipid structures that may be insoluble in aqueous on their own.

Incorporation of a given NP material into a biosensing configuration can allow for exploitation of a specific signal transduction modality such as those based on magnetics, plasmonics, and fluorescence along with FRET depending upon the NP's unique physicochemical and quantum confined properties.

One can substitute a long-lifetime luminescent donor such as a Tb-chelate for the dye molecule. This can allow the sensor to be applied extra/intracellularly or even in vivo while minimizing direct background signal It is possible to engineer a key ester group which can be recognized by lipase in a dye-labeled peptide to be used as a substrate. In the presence of lipase, the ester group is recognized and cleaved by the enzyme releasing the acceptor dye altering the rate of FRET in a concentration and enzyme activity dependent manner.

The design is equally viable with a dye or dark quencher attached to the peptidyl portion if the NP is luminescent.

The NP can act as a quencher, such as in the example of a gold NP.

Substrate can be lyophilized and stored for long periods of time and then reconstituted prior to use and assembly to NPs.

The entire molecular substrate can be synthesized with appropriately-modified peptidyl chemistry.

The biosensor design is amenable to multiplexed formats where different target molecules beyond esters (peptide sequences for proteases, for example) can be similarly adapted and displayed on the same NP entity with a different dye-acceptor. This would allow for monitoring of coupled enzyme activity.

Other materials, such as DNA nanostructures, semiconductor nanoplatelets, and gold NPs exist that can be similarly utilized for substrate immobilization in an analogous 3-dimensional nanoscale architecture.

The peptide domains might be varied. For example, the nanoparticle association domain can be a polyhistidine tag of any suitable length, or it could provide a different form of attachment of the peptide to the nanoparticle, such as 1-ethyl-3-[3-dimethylaminopropyl]carbodiimide hydrochloride (EDC) for crosslinking a carboxyl group to a primary amine. Other possible conjugation protocols for the nanoparticle association domain are known to one of ordinary skill in the art, and include maleimide or dithiol exchange, diazonium salt chemistry, and the like. In another embodiment, the nanoparticle association domain comprises a plurality of either positively- or negatively-charged amino acid residues, so that the peptide is electrostatically attracted to a payload having an opposing charge Concluding Remarks Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

References

1. Algar, W. R., T. Jeen, M. Massey, W. J. Peveler and J. Asselin (2019). "Small Surface, Big Effects, and Big Challenges: Toward Understanding Enzymatic Activity at the Inorganic Nanoparticle-Substrate Interface." *Langmuir* 35(22): 7067-7091.
2. Algar, W. R., A. P. Malanoski, K. Susumu, M. H. Stewart, N. Hildebrandt and I. L. Medintz (2012). "Multiplexed Tracking of Protease Activity Using a Single Color of Quantum Dot Vector and a Time-Gated Forster Resonance Energy Transfer Relay." *Analytical Chemistry* 84(22): 10136-10146.
3. Algar, W. R., A. Malonoski, J. R. Deschamps, J. B. Banco-Canosa, K. Susumu, M. H. Stewart, B. J. Johnson, P. E. Dawson and I. L. Medintz (2012). "Proteolytic Activity at Quantum Dot-Conjugates: Kinetic Analysis Reveals Enhanced Enzyme Activity and Localized Interfacial "Hopping"." *Nano Letters* 12(7): 3793-3802.
4. Blanco-Canosa, J. B., M. Wu, K. Susumu, E. Petryayeva, T. L. Jennings, P. E. Dawson, W. R. Algar and I. L. Medintz (2014). "Recent progress in the bioconjugation of quantum dots." *Coordination Chemistry Reviews* 263: 101-137.
5. Breger, J. C., E. Oh, K. Susumu, W. P. Klein, S. A. Walper, M. G. Ancona and I. L. Medintz (2019). "Nanoparticle Size Influences Localized Enzymatic Enhancement-A Case Study with Phosphotriesterase." *Bioconjugate Chemistry* 30(7): 2060-2074.
6. Chahinian, H. and L. Sarda (2009). "Distinction Between Esterases and Lipases: Comparative Biochemical Properties of Sequence-Related Carboxylesterases." *Protein and Peptide Letters* 16(10): 1149-1161.
7. Diaz, S. A., J. C. Breger and I. L. Medintz (2016). Monitoring Enzymatic Proteolysis Using Either Enzyme- or Substrate-Bioconjugated Quantum Dots. *Rational Design of Enzyme-Nanomaterials*. C. V. Kumar. 571: 19-54.

Gemmill, K. B., J. R. Deschamps, J. B. Delehanty, K. Susumu, M. H. Stewart, R. H. Glaven, G. 8. P. Anderson, E. R. Goldman, A. L. Huston and I. L. Medintz (2013). "Optimizing Protein Coordination to Quantum Dots with Designer Peptidyl Linkers." *Bioconjugate Chemistry* 24(2): 269-281.
9. Grabner, G. F., R. Zimmermann, R. Schicho and U. Taschler (2017). "Monoglyceride lipase as a drug target: At the crossroads of arachidonic acid metabolism and endocannabinoid signaling." *Pharmacology & Therapeutics* 175: 35-46.
10. Guerrand, D. (2017). "Lipases industrial applications: focus on food and agroindustries" *Oilseeds & fats Crops and Lipids* 24: D403.
11. Heeren, J. and O. Bruns (2012). "Nanocrystals, a New Tool to Study Lipoprotein Metabolism and Atherosclerosis." *Current Pharmaceutical Biotechnology* 13(2): 365-372.
12. Hube, B., F. Stehr, M. Bossenz, A. Mazur, M. Kretschmar and W Schafer (2000). "Secreted lipases of *Candida albicans*: cloning, characterisation and expression analysis of a new gene family with at least ten members." *Archives of Microbiology* 174(5): 362-374.
13. Jeen, T. and W. R. Algar (2018). "Mimicking Cell Surface Enhancement of Protease Activity on the Surface of a Quantum Dot Nanoparticle." *Bioconjugate Chemistry* 29(11): 3783-3792.
Johnson, K. A. and R. S. Goody (2011). "The Original Michaelis Constant: Translation of the 1913 Michaelis-Menten Paper." *Biochemistry* 50(39): 8264-8269.
14. Prasuhn, D. E., J. R. Deschamps, K. Susumu, M. H. Stewart, K. Boeneman, J. B. Blanco-Canosa, P. E. Dawson and I. L. Medintz (2010). "Polyvalent Display and Packing of Peptides and Proteins on Semiconductor Quantum Dots: Predicted Versus Experimental Results." *Small* 6(4): 555-564.
15. Ribeiro, B. D., A. M. de Castro, M. A. Z. Coelho and D. M. G. Freire (2011). "Production and Use of Lipases in Bioenergy: A Review from the Feedstocks to Biodiesel Production." *Enzyme Research* 2011: 615803.
16. Sapsford, K. E., D. Farrell, S. Sun, A. Rasooly, H. Mattoussi and I. L. Medintz (2009). "Monitoring of enzymatic proteolysis on a electroluminescent-CCD microchip platform using quantum dot-peptide substrates." *Sensors and Actuators B-Chemical* 139(1): 13-21.
17. Susumu, K., L. D. Field, E. Oh, M. Hunt, J. B. Delehanty, V. Palomo, P. E. Dawson, A. L. Huston and I. L. Medintz (2017). "Purple-, Blue-, and Green-Emitting Multishell Alloyed Quantum Dots: Synthesis, Characterization, and Application for Ratiometric Extracellular pH Sensing." *Chemistry of Materials* 29(17): 7330-7344.
18. Susumu, K., E. Oh, J. B. Delehanty, J. B. Blanco-Canosa, B. J. Johnson, V. Jain, W J. Hervey, W R. Algar, K. Boeneman, P. E. Dawson and I. L. Medintz (2011). "Multifunctional Compact Zwitterionic Ligands for Preparing Robust Biocompatible Semiconductor Quantum Dots and Gold Nanoparticles." *Journal of the American Chemical Society* 133(24): 9480-9496.
19. Skjøt, M., Leonardo De Maria, L., Chatterjee, R., Svendsen, A., Patkar, S. A., Østergaard, P. R., Brask, J. (2009) Understanding the Plasticity of the α/β Hydrolase Fold: Lid Swapping on the *Candida antarctica* Lipase B Results in Chimeras with Interesting Biocatalytic Properties. *ChemBioChem* 10 (10): 520-527.

What is claimed is:

1. A biosensor comprising a quantum dot (QD) and at least one construct adhered to the QD, wherein the construct comprises a peptide, a fluorophore acceptor configured as a Förster resonance energy transfer (FRET) acceptor to the QD and a cleavable ester positioned between the peptide and the fluorophore acceptor, wherein the peptide comprises an amino acid sequence of SEQ ID NO:1, including a nanoparticle association domain effective to bind the construct to the QD; the ester comprises

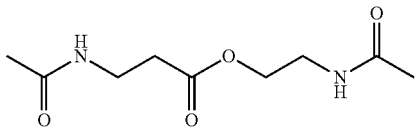

and wherein cleavage of the ester results in dissociation of the QD and the fluorophore acceptor and thus a change in FRET activity.

2. The biosensor of claim 1, wherein the construct is in a state of having the peptide joined to the ester via bis(sulfosuccinimidyl)suberate.

3. The biosensor of claim 1, wherein the ester is cleavable by Lipase B of *Candida antarctica*.

4. A method of measuring esterase activity, the method comprising: contacting a sample with a biosensor, the biosensor comprising a quantum dot (QD) and at least one construct adhered to the QD, wherein the construct comprises a peptide, a fluorophore acceptor configured as a Förster resonance energy transfer (FRET) acceptor to the QD and a cleavable ester positioned between the peptide and the fluorophore acceptor, wherein cleavage of the ester results in dissociation of the QD and the fluorophore acceptor and thus a change in FRET activity; measuring a change in the FRET activity of the biosensor following the contacting; and correlating the change to esterase activity, wherein the peptide comprises an amino acid sequence of SEQ ID NO: 1 including a nanoparticle association domain effective to bind the construct to the OD; and the ester comprises

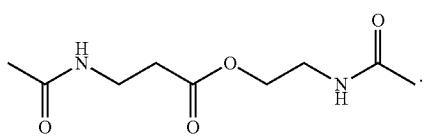

5. The method of claim 4, wherein the esterase is a lipase.

6. The method of claim 4, wherein the construct is in a state of having the peptide joined to the lipid-cleavable ester via bis(sulfosuccinimidyl)suberate.

7. The method of claim 4, wherein the ester is cleavable by Lipase B of *Candida antarctica*.

* * * * *